United States Patent [19]

Anderson et al.

[11] 3,998,215
[45] Dec. 21, 1976

[54] BIO-MEDICAL ELECTRODE CONDUCTIVE GEL PADS

[75] Inventors: Clifford J. Anderson, St. Paul; James T. Gumbusky, South St. Paul, both of Minn.

[73] Assignee: Minnesota Mining and Manufacturing Company, St. Paul, Minn.

[22] Filed: Apr. 23, 1971

[21] Appl. No.: 136,768

Related U.S. Application Data

[63] Continuation-in-part of Ser. No. 784,734, Dec. 18, 1968, abandoned.

[52] U.S. Cl. .................... 128/2.06 E; 128/DIG. 4; 128/417; 128/418
[51] Int. Cl.² .......................................... A61B 5/04
[58] Field of Search ............ 128/2.06, DIG. 4, 268, 128/417, 418; 252/518, 521

[56] References Cited
UNITED STATES PATENTS

| | | | |
|---|---|---|---|
| 2,555,037 | 5/1951 | Jensen | 128/417 |
| 2,887,112 | 5/1959 | Smith | 128/417 |
| 2,943,628 | 7/1960 | Howell | 128/418 |
| 3,027,333 | 3/1962 | Friedman | 252/521 |
| 3,048,549 | 8/1962 | Adams | 252/518 |
| 3,085,577 | 4/1963 | Berman et al. | 128/418 |
| 3,151,619 | 10/1964 | Sullivan | 128/417 |
| 3,249,109 | 5/1966 | Maeth et al. | 128/268 |
| 3,265,638 | 8/1966 | Goodman et al. | 252/518 |
| 3,340,868 | 9/1967 | Darling | 128/2.06 E |
| 3,420,223 | 1/1969 | Day et al. | 128/2.06 E |

FOREIGN PATENTS OR APPLICATIONS 675,494   12/1963   Canada ................. 128/417

*Primary Examiner*—Kyle L. Howell
*Attorney, Agent, or Firm*—Alexander, Sell, Steldt & DeLaHunt

[57] ABSTRACT

A gel pad has impregnated in a porous matrix or held within a cavity, an electrically conductive hydrogel capable of transferring electrical signals between the human body and an electrode of an electrical sensing device when the hydrogel is in contact with the body surface. The hydrogel is lightly adherent to the body surface but sufficiently cohesive so that no residue remains when the pad is removed therefrom.

8 Claims, 7 Drawing Figures

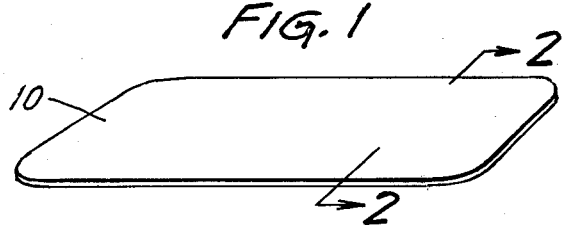
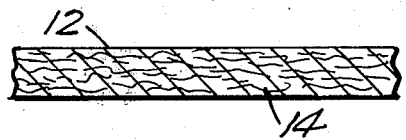
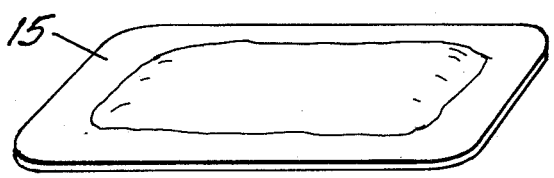
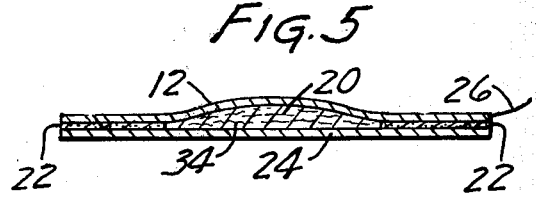
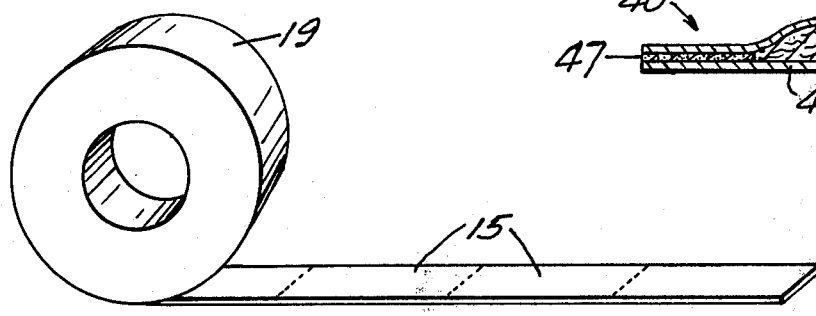
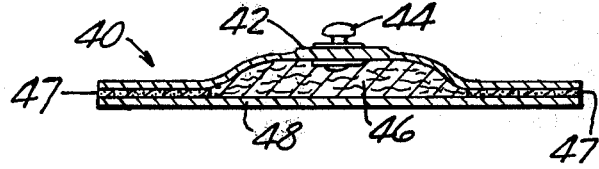
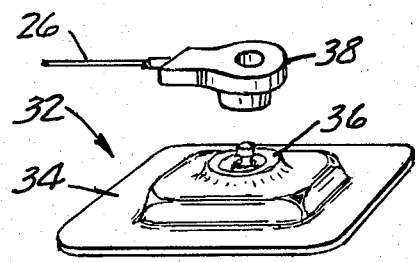

BIO-MEDICAL ELECTRODE CONDUCTIVE GEL PADS

BACKGROUND OF THE INVENTION

This application is a continuation-in-part of copending application Ser. No. 784,734, filed Dec. 18, 1968 now abandoned.

The present invention relates generally to electrically conductive gel pads which are used to carry an electrical signal from the human skin, through a conductive gel on to an electrode attached to an electrical recording device or vice versa. The gel pads have the distinct advantage of forming an intimate contact with the skin thus providing the necessary electrical interface between the skin and the electrode and does this without leaving an objectionable residue upon removal of the pad. The gel pads have light adherent properties and may also be adapted for substantially continuous application to the body for long term diagnostic use, permitting the transfer of electrical signals to and from the body, for diagnosis and other functions, while the patient may perform his daily activities and bodily functions.

There are many different types of electrical conducting devices which are presently being used in medicine, especially in electrocardiography and electroencephalography. A substantially uniform contact between the metal electrode and the skin is necessary to prevent "electrical noise" due to minute spaces between the electrode and skin. This type of "noise" may substantially change the accuracy of a reading. In order to have uniform contact with the skin area, a jelly or cream from a jar or a tube is applied to the area of the device which is to come in contact with the skin. Although these creams and jellys adequately perform the function of a conductive interface between standard medical electrodes and the skin of a patient, the creams and jellys have two destinct disadvantages. First, the individual applying the electrode to the patient must also apply the cream or jelly to the electrode and skin resulting in a residue on the hands of the technician and secondly, a messy residue remains on the skin of the patient and on the electrode after removal which necessitates cleanup of the patient and the electrodes, such cleanup usually requiring a soap or solvent wash after electrode removal from the skin. Similarly, an electrode employed in long term diagnostic use also requires an application of jelly or cream to the underside of the electrode to provide a conductive interface between the skin and electrode which necessitates cleanup.

SUMMARY OF THE INVENTION

The gel pad of the instant invention provides a conductive, conformable interface between the skin and the electrodes placed thereon thus preventing an electrical noise interference and, additionally, a conformable conductor that is easy to apply, aesthetically more acceptable than messy creams or jellys, and requiring no need for cleanup of the equipment operator, patient or equipment after use. The objects and advantages of the present invention will be more widely understood with reference to the accompanying drawings wherein:

FIG. 1 is a perspective view of a hydrogel impregnated pad of the invention;

FIG. 2 is a cross-sectional view of FIG. 1;

FIG. 3 is a perspective view of a gel pad of the invention having a peel off covering of metal foil;

FIG. 4 is a perspective view of a series of metal foil covered gel pads stored in a roll for dispensing;

FIG. 5 is a cross-sectional view of a long term diagnostic gel pad;

FIG. 6 is a cross-sectional view of a long term diagnostic gel pad employing the pad of FIG. 1; and FIG. 7 is a perspective view of a long term diagnostic gel pad having a male-female attachment of the electrode to the gel pad.

Referring now to the drawings for a detailed consideration of the gel pad, FIG. 1 shows the general structure of a short term diagnostic gel pad designated by the number 10. In FIG. 2, the hydrogel 14 is impregnated in and carried by the porous matrix 12 in the form of a fabric or pad, e.g., rayon, cotton, cellulose acetate, cheesecloth, plastic sponge or foam, so that a hydrogel surface is presented on both sides of the pad. A non-woven fabric of rayon or the like as illustrated in the drawing provides an excellent absorbent carrier. The term "hydrogel" as used herein means a high water content gel and is defined in Hackh's Chemical Dictionary, Fourth Edition, Grant, 1969, page 332, as "a gel produced by the coagulation of a colloid with the inclusion of water." Any material that has a porosity sufficient to hold a hydrogel in its matrix may, however, be employed. All that is required is that the material has adequate wet strength and is one that is sufficiently flexible to prevent fracture of the gel upon bending. Being lightly adherent, (but still more cohesive than adhesive) the hydrogel is capable of causing the pad to adhere slightly to the skin on one side and to an electrode on the other. The hydrogel in the pad is sufficiently cohesive so that the electrode may easily be removed from the gel pad without any residue of jelly or cream on the electrode and, additionally, the gel pad may easily be removed from the human skin so that no objectionable residue remains on the patient which requires cleaning. The pad may then be conveniently discarded thus making the whole process of attaching electrical leads to various body areas more economical, more efficient and cleaner than any prior art pads known to applicant.

In another embodiment, the gel pad may be prepared simply by reinforcing the hydrogel with fiber supports. The fibrous support adds structural integrity to the gels so that the gel pad can be removed from the skin intact without leaving a residue. Fibers of rayons, dacron, cotton, glass wool, paper pulp. wool, etc., may be used. The length of the fibers should be sufficient so that there is overlapping of the fibers within the gel to impart sutructural integrity. Preferably, the fibers are about ¾ inch in length. Fiber content of the gel pad can be from 0.5 to 10% by weight and preferably 1.3% by weight.

The gel pad or a plurality of gel pads may be sealed in individual aluminum foil packages 15 as shown in FIG. 3 to prevent the evaporation of water and to aid in the ease of handling when being used or stored. It is to be understood that any material may be used for the package which is impermeable to moisture and easily removable so that the gel pad might conveniently be removed for use. These individual pads, covered by foil, may be individually packaged and the packages separably connected to one another as by score lines 17 or the like, in the form of a continuous strip wound into a roll 19 for ease of dispensing as shown in FIG. 4. Each foil section containing a gel pad is separated by numerous perforations in a straight line so that an individual pad may be torn off and separated from the rest.

When an electrically conductive interface is needed as in the taking of an electrocardiogram (ECG), the pad is removed from the protective foil and placed on the desired lead site on the patient causing the hydrogel on the pad surface to contact (wet) and lightly adhere to the skin. An electrode from a readout device is placed on the exposed hydrogel surface of the pad and the recording is then taken. Afterwards the pad is removed from the skin and the electrode, leaving no residue or film on either, and discarded.

The pad may be easily prepared by dipping a porous webbed material into an aqueous solution of hydrogel former, e.g., polyvinyl alcohol, to wet the material, scraping off the excess solution and then dipping into a solution of gel forming agent or a cross-linker for the gel former and thereby forming a gel throughout the webbed material. The reinforced hydrogel pad may also be prepared by extruding a thin layer of the gel, depositing a sufficient amount of supporting fibers over the surface of that layer and extruding a second layer of gel over the fibers. Calendaring of this combination promotes gel contact through the fiber layer.

The porosity of the support or carrier material can range from that of a plain mat of fibers in the gel (very high porosity) to that of a fibrous fabric support which exhibits considerable resistance to air flow, a property measured on a Gurley Densometer. Certain non-woven fabrics and fibers exhibit no resistance to air flow and thus result in readings on the densometer equal to that of the device with no sample (300 cc. of air passing through in 0.1 seconds). Other support webs from which the gel pad of the present invention have been prepared give readings up to about 300 cc. of air in 20 seconds. In the preferred embodiment, the support or carrier exhibits a reading of 300 cc. of air in 0.2 seconds. The support should have a Gurley Densometer reading of 300 cc. of air passing through in from about 0.1 to 50 seconds.

The tensile strength of the support material or carrier is not crucial as long as the above porosity criteria is met. The support or carrier could range from a mat of fibers with near 0 tensile strength to materials such as non-woven webs reinforced with rayon fibers exhibiting tensile strengths in excess of 20 pounds per square inch, tested on an Instron tester. Preferably, the supporting structure incorporates a non-woven web with a tensile strength of about 4 pounds per square inch of the width.

The stiffness of the support or carrier is more important than the tensile strength, as a very stiff support will not provide good performance under suction electrodes. These are electrodes that are held on the skin by a suction against the skin created in the cup-like electrode. A mat of separate fibers exhibits essentially no stiffness whereas a paper or non-woven web exhibits some stiffness. One method for testing such stiffness is described in the ASTM Federal Test Methods Standard No. 191, Method 5204 31 December, 1968 entitled: "Stiffness of Cloth, Directional; Self-Weighted Cantilever Method". Using the procedures described therein, it was found that a stiffness of about 25 to 250 millimeters as defined in the above method, could be used without problems in suction cup adherence to the skin. Preferably, the support or carrier has a stiffness of about 55 millimeters.

In the absence of a standard method for measuring the viscosity of the hydrogel usable in the present invention, the viscosity of the gel was tested by using open mouth bottles having a 16 ounce capacity and 89 millimeter cap, and a stainless steel ball having a ⅞ inch diameter and a weight of 45.68 grams. The ball was placed on the surface of the sample in the middle of the bottle. Times were recorded for the ball to settle between two marks on the bottle (30 millimeters apart vertically), and the results were reported as time/30 millimeters. It wwas found that gels having a viscosity, as measured according to the above procedure, having values of from about 2 to 4000 seconds/30 millimeters, and preferably 1000 seconds/30 millimeters, were suitable for most applications. The preferred viscosity of 1000 seconds/30 millimeters represented the viscosity of the preferred 5% polyvinyl alcohol gel.

The gel pad of the present invention should have a thickness of from about 5 to 50 mils and preferably 25–30 mils (0.025–0.030 inches). However, the pads have been shown to be effective when, through successive coatings, thicknesses in excess of 100 mils (0.1 inch) are made.

For purposes of conduction, it was found that preferably the volume resistivities could range from about $3 \times 10^4$ ohm-cm to about $4.5 \times 10^4$ ohm-cm. Volume resistivity is the reciprocal of conductivity. With other gels, such as agar, guar gum, alginates, and the like, conductivity can be varied substantially by the type and amount of the salt employed. The above preferred volume resistivities relate to the PVA gels employing a sodium borate salt to increase conductivity. Any non-toxic salt capable of ionization could be used, such as sodium chloride, potassium chloride, sodium sulfate, etc. With the other gels mentioned heretofore, the volume resistivity will be related to the amount of salt added. Thus, the values could range from about 5 ohm-cm to several thousand ohm-cm. As would be expected, the volume resistivity of the gels will be more than that of an aqueous solution with an equal salt concentration as the viscosity of the gel tends to hamper ion mobility.

The long term diagnostic gel pad illustrated in FIG. 5 has a top metal foil layer 18 covering the top surface. Although aluminum foil is preferred as the top surface, any material which is impermeable and sufficiently flexible so that it may bend with various body movements, may be used. The foil layer is designed so that the center is elevated forming a cavity or inverted hole immediately below the center of the foil layer. On the underside of the foil layer and on its periphery is a layer of pressure-sensitive adhesive 22 which causes the pad to adhere to the skin surface when applied thereto. Immediately below the pressure-sensitive adhesive is a release liner 24 which protects the pressure-sensitive adhesive and also forms the bottom surface of the total gel pad thereby defining a cavity 34 therein. The hydrogel 20, which is the conductor of the electrical impulse is located in the cavity 34 but not impregnated in the cavity walls. A contact or wire 26 is attached to the foil layer and when in use, has the other end attached to an electrical recording device. In long term diagnostic use, the gel pad will remain on the skin for a long period of time and the recording device may be carried by the patient or attached to him by some means. Due to this time period, the pad must be comfortable, as the patient will want to continue to carry on with his daily routine without noticeable irritation. Bearing this in mind, the materials used in this invention are at least flexible enough so that normal body movements may be carried out without an effect on the pad or patient.

Furthermore, it is important that the pad has appropriate aesthetic properties as it may be exposed some of the time.

When the conductive pad is ready to be used, the release liner 24 is peeled away exposing the hydrogel and the pressure-sensitive adhesive 22 which is pressed against the skin at the selected lead site allowing the hydrogel to come in contact with the skin. The hydrogel 20 remains within the pad, lightly attached to it. Essentially none of the hydrogel comes off with the release liner as the cohesive property of the hydrogel is stronger than its adhesive attachment to the liner and therefore remains together. The lead wire 26 is then attached to a wire from the recording device. Additional means may be used to hold the pad on to insure adherence such as adhesive tape. After recording, the wires are detached and the pad removed without leaving objectionable residue on the patient's skin and therefore requiring no cleanup.

Additionally, a porous web (not shown) impregnated with a hydrogel may be interposed between the release liner 24 and the foil layer 18 used to form the lower surface of the pad and to aid in retaining the hydrogel within the cavity. In this situation the impregnated web would be attached to the peripheral area of the under surface of the impermeable foil layer 18 by the pressure-sensitive adhesive to adhere the pad to the skin by other means. The impregnated web would serve to hold the hydrogel in the cavity and also aid in the conduction of an electrical signal between the skin and the electrode.

Another embodiment of the long term diagnostic pad is shown in FIG. 6. The pad 40 comprises a hydrogel impregnated non-woven porous pad 46 having an impermeable upper surface 42 which covers the hydrogel pad 46 and extends slightly beyond near the lower portion of the pad but level with the bottom of the hydrogel pad. Attached to this extending portion is a layer of pressure-sensitive adhesive 47 which is covered by a release liner 48. A wire or fastener 44 is attached to the inner hydrogel pad 46 or at least comes in contact with the hydrogel surface and extends through the impermeable surface layer to the exterior of the entire pad where it may be attached to an electrode.

Various means of connecting a lead wire to the pad may be used. In FIG. 7, another form of long term diagnostic pad is illustrated. This pad 32 has a backing or top layer 34 of impermeable material with a central male conductive fastener part 36 projecting therefrom. The electrode 38 comprises the female portion of the snap fastener and these may conveniently be snapped together to complete the connection when the pad is to be used.

The following examples will serve to illustrate the preparation of a typical conductive gel pad of the invention, wherein all parts are by weight unless otherwise stated.

EXAMPLE I

A roll of porous non-woven fabric of suitable wet strength is treated with an emulsion of an acrylate polymer commercially available as Rohm & Haas HA-8. The fabric is led on a series of rollers through a bath solution of 4% polyvinyl alcohol and 0.1% 1-(3-chloroallyl)-3,5,7-triaza- 1-azoniaadamantane chloride, which is a fungicide (commercially available as Dowicil 100), in water. The solution wets the fabric and the excess solution is scraped off the moving web with a rubber scraper knife before the web enters a second bath. The fabric need only be submerged in the polyvinyl alcohol solution for about one second. The moving web then enters a second bath which contains 10% sodium borate decahydrate in water. The temperature should be kept above 30° °C. The sodium borate decahydrate serves as a cross-linking agent or gelling agent for the polyvinyl alcohol forming a gel throughout the fabric as the web emerges from the second solution. The time of immersion was about 1 second. The gel impregnated pad is cut into squares and is ready to be used. The gel pad was used as a conductive interface between standard electro-cardiographic electrodes and the skin of a test patient. The recordings obtained were of equal quality to those resulting from the use of creams and jellies in current ECG techniques with the additional advantage that no residue remained on the patient's skin or on the electrode when the pad was removed.

EXAMPLE II

The same procedure as described in Example I was used. However, only one solution was used which contained 1% by weight of agar (Ionagar No. 2) and 0.1% 1-(3-chloroallyl)- 3,5,7-triaza-1-azoniaadamantane chloride as a fungicide. The agar was heated to boiling in a 2% NaCl solution in water. The web was passed through the warm solution and after a very short cooling period of about one or two minutes a gel formed which was carried by the matrix of the porous non-woven pad. The pad was tested as an electrical interface and results were obtained similar to those in Example I.

Although the combination of Example I is preferred, various gels may be used satisfactorily in the instant gel pad. Examples of such gels are guar gum, agars, alginates and the above gel with various concentrations of polyvinyl alcohol.

EXAMPLE III

A reinforced hydrogel gel pad was prepared from a gel composed of 5% by weight polyvinyl alcohol, 3% by weight potassium tetraborate, and 92% by weight water, which gel was extruded into thin sheets. Rayon fiber staple (¾ inch, 1½ denier) was spread uniformly over the gel surface of one layer. The second layer of gel was extruded over the deposited fibers and the resulting three-layered material was then calendared to promote gel contact through the fiber layer. The fiber content was 1.3% by weight. The resulting material was cut into pieces 1½ × 2½ inch and a piece was placed on the skin. The gel pad exhibited good structural integrity and could be removed intact from the skin with no residue left thereon.

What is claimed is:

1. An electrically conductive pad conformable to the surface of the human body and adapted to facilitate the transfer of electrical signals between the body and an electrode, comprising a porous, fibrous carrier having a lightly adherent, conductive hydrogel carried thereby, said hydrogel impregnating and surfacing both sides of said carrier and said hydrogel being more cohesive to said hydrogel than adhesive to the surface of the human body to enable residue-free removal from the skin.

2. The pad of claim 1 wherein said porous, fibrous carrier is a fabric carrier having a substantially porous matrix.

3. The pad of claim 2 wherein said fabric carrier is an absorbent, non-woven fabric.

4. The pad of claim 1 wherein said hydrogel comprises a mixture of water, polyvinyl alcohol, sodium borate decahydrate and a fungicide, said water being present in a concentration of at least about 70% by weight.

5. The pad of claim 1 wherein said carrier has a porosity of from about 300 cc. of air in 0.1 to 50 seconds as measured on a Gurley Densometer and a volume resistivity of from about 5 ohm-cm to 50,000 ohm-cm.

6. The pad of claim 5 wherein said hydrogel comprises a mixture of water, polyvinyl alcohol, sodium borate decahydrate and a fungicide, said water being present in a concentration of at least about 70% by weight.

7. The pad of claim 5 wherein said fibers are rayon fibers.

8. An electrically conductive pad conformable to the surface of the human body and adapted to facilitate the transfer of electrical signals between said body and an electrode, comprising a thin layer of a reinforced, lightly adherent, conductive hydrogel reinforced with from about 0.5 to 10% by weight of a fibrous material, said hydrogel being available for contact with the skin on at least two sides, said hydrogel being more cohesive to said hydrogel than adhesive to the surface of the human body to enable residue-free removal from the skin.

* * * * *